US00PP15918P2

(12) United States Plant Patent
Boekestijn-Vermeer

(10) Patent No.: US PP15,918 P2
(45) Date of Patent: Aug. 9, 2005

(54) ***PELARGONIUM* PLANT NAMED 'BONTROSAI'**

(50) Latin Name: *Pelargonium graveolens*
Varietal Denomination: Bontrosai

(75) Inventor: Klazina Boekestijn-Vermeer, Naaldwijk (NL)

(73) Assignee: Pedro Plant, Naaldwijk (NL)

( * ) Notice: Subject to any disclaimer, the term of this patent is extended or adjusted under 35 U.S.C. 154(b) by 7 days.

(21) Appl. No.: 10/932,275

(22) Filed: Sep. 1, 2004

(51) Int. Cl.[7] ..... A01H 5/00
(52) U.S. Cl. ..... Plt./324
(58) Field of Search ..... Plt./324

*Primary Examiner*—Kent Bell
(74) *Attorney, Agent, or Firm*—C. A. Whealy

(57) ABSTRACT

A new and distinct cultivar of *Pelargonium* plant named 'Bontrosai', characterized by its upright, columnar and compact growth habit; leaves arranged spirally and positioned perpendicular to the stem; leaves roughly palmate, deeply lobed, reflexed, globular in shape and citron-scented.

2 Drawing Sheets

Botanical classification/cultivar designation: *Pelargonium graveolens* cultivar Bontrosai.

BACKGROUND OF THE INVENTION

The present invention relates to a new and distinct cultivar of *Pelargonium* plant, commercially known as a scented Geranium, botanically known as *Pelargonium graveolens,* and hereinafter referred to by the name 'Bontrosai'.

The new *Pelargonium* is a naturally-occurring whole plant mutation of an unnamed selection of *Pelargonium graveolens,* not patented. The new *Pelargonium* was discovered and selected as a single plant within a population of plants of the unnamed parent selection by the Inventor on Mar. 15, 2002 in a controlled environment in The Hague, The Netherlands.

Asexual reproduction of the new *Pelargonium* by tissue culture in Piaseczno, Warsawa, Poland, since May 2, 2002 has shown that the unique features of this new *Pelargonium* are stable and reproduced true to type in successive generations of asexual reproduction.

SUMMARY OF THE INVENTION

The following traits have been repeatedly observed and are determined to be the unique characteristics of 'Bontrosai'. These characteristics in combination distinguish 'Bontrosai' as a new and distinct *Pelargonium* cultivar:

1. Upright, columnar and compact growth habit.
2. Leaves arranged spirally and positioned perpendicular to the stem.
3. Leaves roughly palmate, deeply lobed, reflexed and globular in shape.
4. Leaves citron-scented.

Plants of the new *Pelargonium* can be compared to plants of the parent selection. In side-by-side comparisons conducted in Hannover, Germany, plants of the new *Pelargonium* and the parent selection differed in the following characteristics:

1. Plants of the new *Pelargonium* were upright and not branching whereas plants of the parent selection were freely branching.

2. Plants of the new *Pelargonium* were slower growing than plants of the parent selection.
3. Leaves of plants of the new *Pelargonium* were darker green in color than leaves of plants of the parent selection.
4. Leaves of plants of the new *Pelargonium* were reflexed whereas leaves of plants of the parent selection were flat.

Plants of the new *Pelargonium* can also be compared to plants of the *Pelargonium graveolens* cultivar Citrosa, not patented. In side-by-side comparisons conducted in Hannover, Germany, plants of the new *Pelargonium* and the cultivar Citrosa differed in the following characteristics:

1. Plants of the new *Pelargonium* were upright and not branching whereas plants of the cultivar Citrosa were freely branching.
2. Plants of the new *Pelargonium* were narrower than plants of the cultivar Citrosa.
3. Plants of the new *Pelargonium* were slower growing than and not as vigorous as plants of the cultivar Citrosa.
4. Plants of the new *Pelargonium* had longer internodes than plants of the cultivar Citrosa.
5. Stems of plants of the new *Pelargonium* were darker green in color than stems of plants of the cultivar Citrosa.
6. Leaves of plants of the new *Pelagonium* were smaller and had narrower petioles than leaves of plants of the cultivar Citrosa.
7. Leaves of plants of the new *Pelargonium* were darker green in color than leaves of plants of the cultivar Citrosa.
8. Leaves of plants of the new *Pelargonium* were reflexed whereas leaves of plants of the cultivar Citrosa were flat.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Flower and foliage colors in the photographs may differ slightly from the color values cited in the detailed botanical description which accurately describe the colors of the new *Pelargonium.*

The photograph on the first sheet comprises a side perspective view of a typical plant of 'Bontrosai' grown in a container.

The photograph on the second sheet comprises a side perspective view of three typical plants of 'Bontrosai' at three different growth stages.

DETAILED BOTANICAL DESCRIPTION

The cultivar Bontrosai has not been observed under all possible environmental conditions. The phenotype may vary somewhat with variations in environment such as temperature and light intensity, without, however, any variance in genotype. The aforementioned photographs and following observations and measurements describe plants grown in Naaldwijk, The Netherlands under commercial practice in a glass-covered greenhouse during the autumn with day temperatures about 20° C., night temperatures about 17° C. and light levels about 40 kilolux. Plants used for the photographs and description were about 14 weeks from planting rooted cuttings and were grown in 12-cm containers. In the following description, color references are made to The Royal Horticultural Society Colour Chart, 1995 Edition, except where general terms of ordinary dictionary significance are used.

Botanical classification: *Pelargonium graveolens* cultivar Bontrosai.

Parentage: Naturally-occurring whole plant mutation of an unnamed selection of *Pelargonium graveolens,* not patented.

Propagation:

*Type.*—By tissue culture.

*Time to initiate roots, summer and winter.*—About two weeks at 21° C.

*Time to produce a rooted young plant, summer.*—About four weeks at 22° C.

*Time to produce a rooted young plant, winter.*—About five weeks at 21° C.

*Root description.*—Fine, fibrous; white in color.

*Rooting habit.*—Freely branching.

Plant description:

*Growth habit and appearance.*—Upright, columnar and compact. Slow-growing and low vigor.

*Branching habit.*—Plants do not branch.

*Plant height* (*to top of foliage*).—About 30.5 cm.

*Plant width.*—About 18 cm.

*Stem description.*—Internode length: About 2.5 cm. Texture: Pubescent. Color: 144A; at nodes of older stems, overlain with close to 187A.

*Foliage description.*—Arrangement: Spirally arranged and positioned perpendicular to the stem; simple. Length: About 5 cm. Width: About 5 cm. Shape: Roughly palmate; deeply lobed; reflexed; globular. Apex: Rounded. Base: Truncate to slightly cordate. Margin: Deeply lobed. Venation: Palmate. Scent: Citron-like. Texture, upper and lower surfaces: Pubescent; glandular. Color: Developing and fully expanded foliage, upper surface: 144A; venation, 144A. Developing and fully expanded foliage, lower surface: 144A to 144B; venation, 144B. Petiole: Length: About 6 cm. Diameter: About 7 mm. Texture, upper and lower surfaces: Pubescent. Color, upper and lower surfaces: 144A; older leaves, faintly overlain with close to 187A.

Flower description: Flower development has not been observed on plants of the new *Pelargonium.*

Disease/pest resistance: Resistance to pathogens and pests common to *Pelargoniums* has not been observed.

Temperature tolerance: Plants of the new *Pelargonium* have been observed to tolerate temperatures from 0 to 35° C.

It is claimed:

1. A new and distinct cultivar of *Pelargonium* plant named 'Bontrosai', as herein illustrated and described.

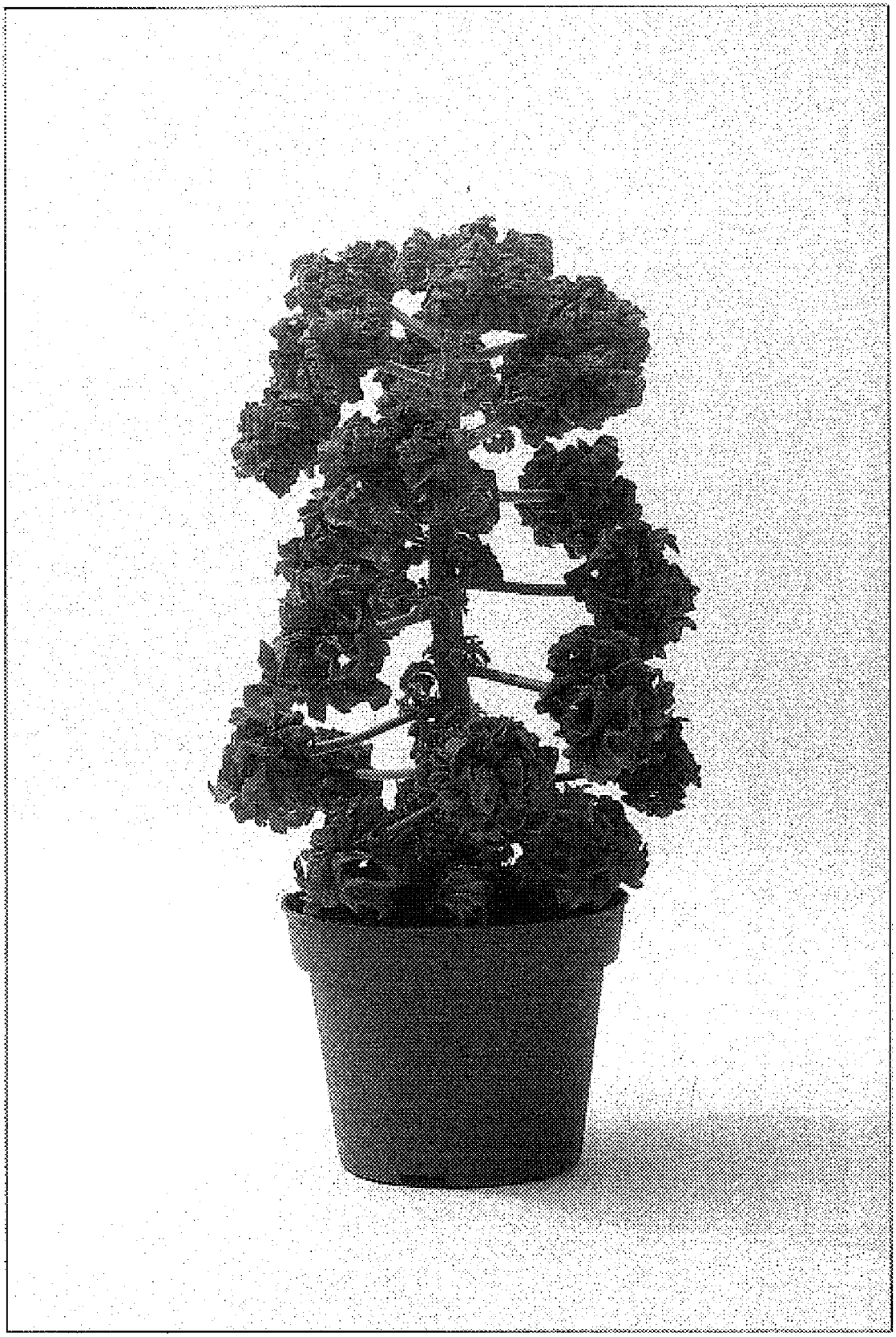

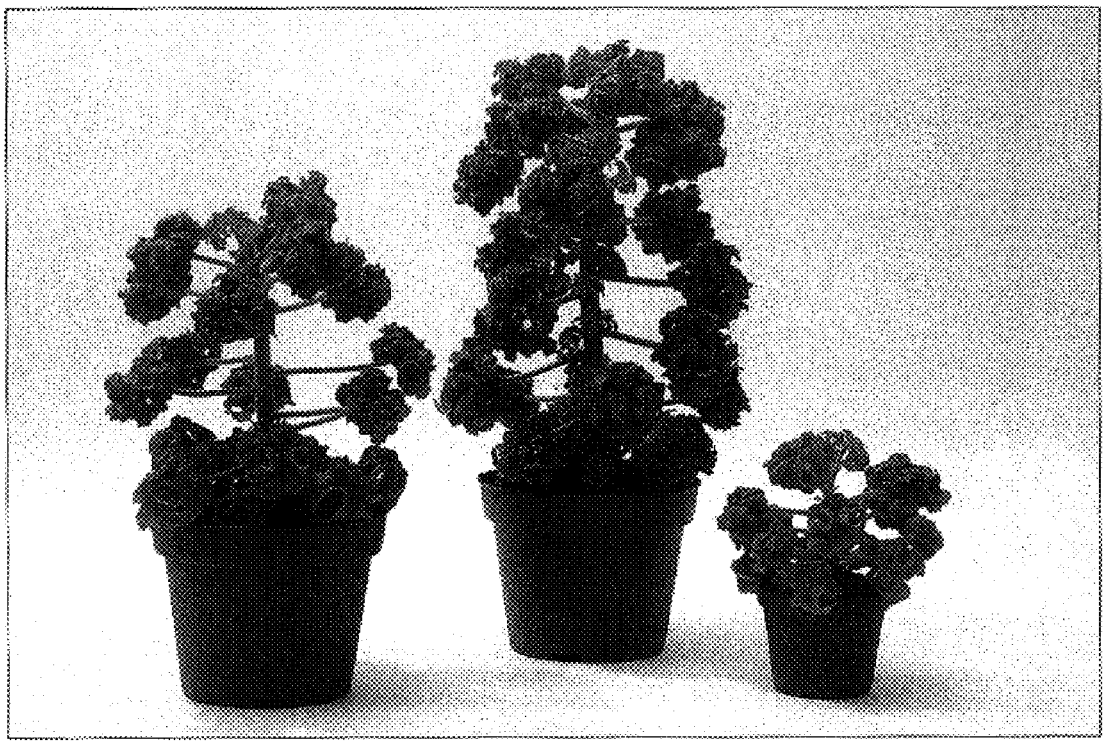

* * * * *